(12) United States Patent
Tagami et al.

(10) Patent No.: US 9,919,141 B2
(45) Date of Patent: Mar. 20, 2018

(54) NEEDLE-SHAPED BODY AND METHOD FOR MANUFACTURING NEEDLE-SHAPED BODY

(71) Applicant: TOPPAN PRINTING CO., LTD., Taito-ku (KR)

(72) Inventors: Hanae Tagami, Taito-ku (JP); Hiroyuki Kato, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 371 days.

(21) Appl. No.: 14/579,490

(22) Filed: Dec. 22, 2014

(65) Prior Publication Data

US 2015/0112283 A1    Apr. 23, 2015

Related U.S. Application Data

(63) Continuation of application No. PCT/JP2013/065984, filed on Jun. 10, 2013.

(30) Foreign Application Priority Data

Jun. 22, 2012  (JP) ................... 2012-140736

(51) Int. Cl.
*A61M 5/32* (2006.01)
*A61M 37/00* (2006.01)
(Continued)

(52) U.S. Cl.
CPC ....... *A61M 37/0015* (2013.01); *A61K 9/0014* (2013.01); *A61K 9/0021* (2013.01);
(Continued)

(58) Field of Classification Search
CPC ........ A61K 9/0021; A61M 2037/0023; A61M 2037/0046; A61M 2037/0053; A61M 37/0015
See application file for complete search history.

(56) References Cited

U.S. PATENT DOCUMENTS 6,440,096 B1 * 8/2002 Lastovich ............ A61B 17/205
424/448
2011/0276028 A1   11/2011 Singh et al.
(Continued)

FOREIGN PATENT DOCUMENTS

EP    2 441 437 A1    4/2012
GB    1 408 925       10/1975
(Continued)

OTHER PUBLICATIONS

Extended European Search Report dated Feb. 12, 2016 in Patent Application No. 13807449.7.
(Continued)

*Primary Examiner* — Rebecca E Eisenberg
(74) *Attorney, Agent, or Firm* — Oblon, McClelland, Maier & Neustadt, L.L.P.

(57) ABSTRACT

A method for manufacturing a needle-shaped body, including supplying a first aqueous solution to an intaglio plate, supplying a second aqueous solution to the intaglio plate, drying the first and second aqueous solutions in the intaglio plate such that a dried body is formed on the intaglio plate, and separating the dried body from the intaglio plate such that a needle-shaped body including a needle-shaped projection and a support base which supports the needle-shaped projection is obtained. The intaglio plate includes a recess corresponding to the needle-shaped projection, the first aqueous solution is supplied to fill at least a portion of the recess, the first aqueous solution and the second aqueous solution are immiscible, the first aqueous solution forms a projection side layer in the needle-shaped body, and the second aqueous solution forms a support base side layer on the projection side layer in the needle-shaped body.

11 Claims, 8 Drawing Sheets

(51) Int. Cl.
   *A61K 9/00* (2006.01)
   *B29C 39/02* (2006.01)
   *B29K 1/00* (2006.01)
   *B29L 31/00* (2006.01)
(52) U.S. Cl.
   CPC ... *B29C 39/026* (2013.01); *A61M 2037/0023* (2013.01); *A61M 2037/0046* (2013.01); *A61M 2037/0053* (2013.01); *B29K 2001/08* (2013.01); *B29L 2031/759* (2013.01)

(56) References Cited

U.S. PATENT DOCUMENTS

2012/0029434 A1* 2/2012 Kobayashi ........ A61M 37/0015
                                                              604/173
2013/0041330 A1   2/2013 Matsudo et al.

FOREIGN PATENT DOCUMENTS

| JP | 48-93192 | 12/1973 |
|----|----------|---------|
| JP | 2010/233674 | 10/2010 |
| WO | 2008/004597 | 1/2008 |
| WO | 2008/013282 | 1/2008 |
| WO | 2008/020632 | 2/2008 |
| WO | WO 2009/048607 A1 | 4/2009 |
| WO | 2011/105508 | 9/2011 |
| WO | 2011/140274 | 11/2011 |
| WO | WO 2011/135531 A2 | 11/2011 |

OTHER PUBLICATIONS

International Search Report dated Aug. 6, 2013, in International Patent Application No. PCT/JP2013/065984.

* cited by examiner

NEEDLE-SHAPED BODY AND METHOD FOR MANUFACTURING NEEDLE-SHAPED BODY

CROSS-REFERENCE TO RELATED APPLICATIONS

The present application is a continuation of International Application No. PCT/JP2013/065984, filed Jun. 10, 2013, which is based upon and claims the benefits of priority to Japanese Application No. 2012-140736, filed Jun. 22, 2012. The entire contents of these applications are incorporated herein by reference.

BACKGROUND OF THE INVENTION

Technical Field

The present invention relates to a method for manufacturing a needle-shaped body and a needle-shaped body.

Background Art

A transdermal absorption method as a method for penetrating a delivery agent such as a medicine from a skin surface and administering the delivery agent into a body has been used as a method that enables easy administration of the delivery agent without causing any pain to a human body.

SUMMARY OF INVENTION

According to one aspect of the present invention, a method for manufacturing a needle-shaped body includes supplying a first aqueous solution to an intaglio plate, supplying a second aqueous solution to the intaglio plate, drying the first and second aqueous solutions in the intaglio plate such that a dried body is formed on the intaglio plate, and separating the dried body from the intaglio plate such that a needle-shaped body including a needle-shaped projection and a support base which supports the needle-shaped projection is obtained. The intaglio plate includes a recess corresponding to the needle-shaped projection, the first aqueous solution is supplied to fill at least a portion of the recess, the first aqueous solution and the second aqueous solution are immiscible, the first aqueous solution forms a projection side layer in the needle-shaped body, and the second aqueous solution forms a support base side layer on the projection side layer in the needle-shaped body.

According to another aspect of the present invention, a needle-shaped body includes a needle-shaped projection, and a support base which supports the needle-shaped projection. At least a portion of the needle-shaped projection includes a projection side layer, at least a portion of the support base includes a support base side layer, and the projection side layer is formed on the support base side layer such that peeling strength between the projection side layer and the support base side layer is 8 N/15 mm in width or lower.

According to still another aspect of the present invention, a needle-shaped body includes a needle-shaped projection, and a support base which supports the needle-shaped projection. At least a portion of the needle-shaped projection includes a projection side layer, at least a portion of the support base includes a support base side layer, the projection side layer is formed on the support base side layer, the projection side layer includes at least one of pullulan and dextran, and the support-base-side-layer includes at least one of hydroxypropyl cellulose, hydroxyethyl cellulose, methyl cellulose, and hydroxypropyl methyl cellulose.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
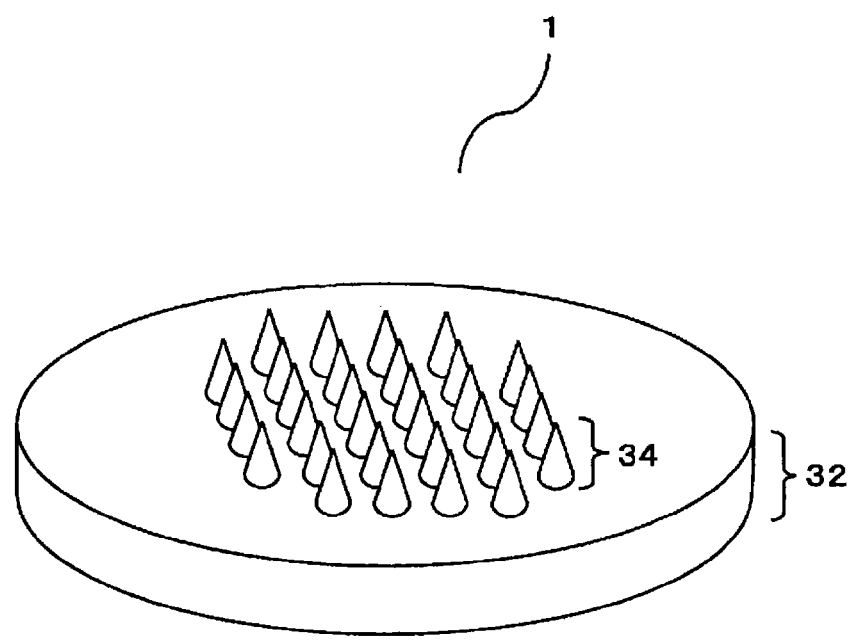
FIG. 1 is a perspective view of a needle-shaped body according to one embodiment of the invention.

The embodiments will now be described with reference to the accompanying drawings, wherein like reference numerals designate corresponding or identical elements throughout the various drawings.

A method for manufacturing a needle-shaped body according to one embodiment of the invention is a method for manufacturing a needle-shaped body that includes a needle-shaped projection and a support base for supporting the projection, the method for manufacturing characterized by including: a process of supplying an aqueous solution of a material forming a projection-side-layer to an intaglio plate having a recess that corresponds to the projection; a process of supplying an aqueous solution of a material forming a support-base-side-layer to the intaglio plate; a process of drying the aqueous solution in the intaglio plate to form the needle-shaped body; and a process of peeling the needle-shaped body from the intaglio plate, in that the aqueous solution of the material forming a projection-side-layer and the aqueous solution of the material forming a support-base-side-layer are a liquid-liquid dispersion system.

With the method for manufacturing a needle-shaped body in this configuration, peeling strength between a projection side layer and a support base side layer of the obtained needle-shaped body can be low, and only the support base side layer can be peeled from a skin in a state that the projection side layer is in contact with the skin after the skin is punctured with the needle-shaped body.

In addition, in the method for manufacturing a needle-shaped body, the peeling strength between the projection side layer and the support base side layer is preferably 8 N/15 mm in width or lower. Since the peeling strength is set to fall within the above range, only the support base side layer can be peeled from the skin in the state that the projection side layer is in contact with the skin after the skin is punctured with the needle-shaped body.

In addition, the method for manufacturing a needle-shaped body preferably includes a process of drying the aqueous solution of the material forming a projection-side-layer in the intaglio plate after the process of supplying the aqueous solution of the material forming a projection-side-layer to the intaglio plate and before the process of supplying the aqueous solution of the material forming a support-base-side-layer to the intaglio plate.

The drying process is provided after the process of supplying the aqueous solution of the material forming a projection-side-layer. Accordingly, compared to a method for manufacturing a needle-shaped body in which the process of supplying the aqueous solution of the material forming a support-base-side-layer to the intaglio plate is performed without drying after the process of supplying the aqueous solution of the material forming a projection-side-layer to the intaglio plate, the method for manufacturing a needle-shaped body can lower the peeling strength between the projection side layer and the support base side layer of the obtained needle-shaped body.

In addition, in the method for manufacturing a needle-shaped body, specific gravity of the aqueous solution of the material forming a projection-side-layer is preferably greater than specific gravity of the aqueous solution of the material forming a support-base-side-layer. By establishing the above magnitude relationship, the peeling strength between the projection side layer and the support base side layer of the obtained needle-shaped body can be low. Especially, in the case where the process of supplying the aqueous solution of the material forming a support-base-side-layer to the intaglio plate is performed without drying after the process of supplying the aqueous solution of the material forming a projection-side-layer to the intaglio plate, so as to manufacture the needle-shaped body, a relation in the specific gravity of the two aqueous solutions is preferably set to the above magnitude relationship. On the other hand, in the case where the drying process is provided after the process of supplying the aqueous solution of the material forming a projection-side-layer, the peeling strength between the projection side layer and the support base side layer of the obtained needle-shaped body can be low even when the specific gravity of the two aqueous solutions does not satisfy the above magnitude relationship.

In addition, in the method for manufacturing a needle-shaped body, it is preferred that the material forming a projection-side-layer contains a material selected from pullulan and dextran, and the material forming a support-base-side-layer contains a material selected from hydroxypropyl cellulose, hydroxyethyl cellulose, methyl cellulose, and hydroxypropyl methyl cellulose. Since the material for forming the each layer is selected from the above materials, the aqueous solution of the material forming a projection-side-layer and the aqueous solution of the material forming a support-base-side-layer can be a liquid-liquid dispersion system, and the peeling strength between the projection side layer and the support base side layer of the obtained needle-shaped body can be low.

Furthermore, the needle-shaped body is a needle-shaped body that includes the needle-shaped projection and the support base for supporting the projection, and is characterized by including at least two layers of the projection side layer and the support base side layer, and in that the peeling strength between the projection side layer and the support base side layer is 8 N/15 mm in width or lower. Since the peeling strength is set to fall within the above range, only the support base side layer can easily be peeled from the skin in the state that the projection side layer is in contact with the skin after the skin is punctured with the needle-shaped body.

Moreover, the needle-shaped body is the needle-shaped body that includes the needle-shaped projection and the support base for supporting the projection, and is characterized by including the at least two layers of the projection side layer and the support base side layer, in that the material forming a projection-side-layer contains the material selected from the group of pullulan and dextran and that the material forming a support-base-side-layer contains the material selected from the group of hydroxypropyl cellulose, hydroxyethyl cellulose, methyl cellulose, and hydroxypropyl methylcellulose. As for the needle-shaped body selected from and formed of any of these materials, the peeling strength between the projection side layer and the support base side layer of the obtained needle-shaped body can be low, and only the support base side layer can be peeled from the skin in the state that the projection side layer is in contact with the skin after the skin is punctured with the needle-shaped body.

A detailed description will be made on an embodiment of the invention by using the drawings. First, a structure and a material of a needle-shaped body will be described, and then a method for manufacturing the needle-shaped body will be described.

Figure 2A:
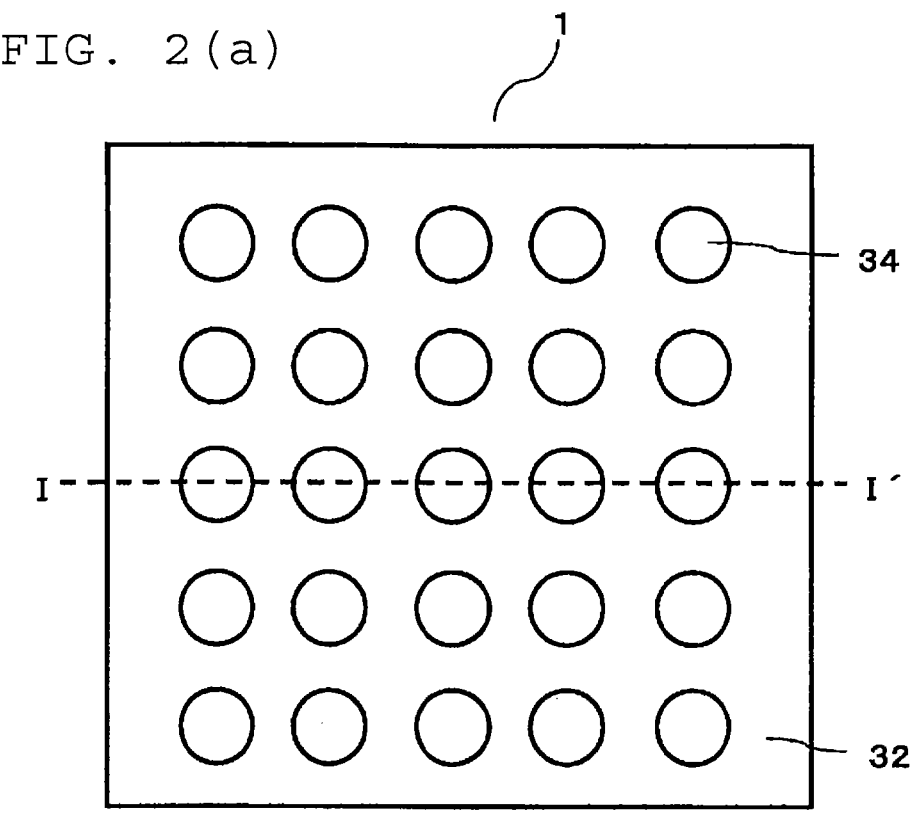
FIG. 2(a) is a top view from the projection side of the needle-shaped body.
Figure 2B:
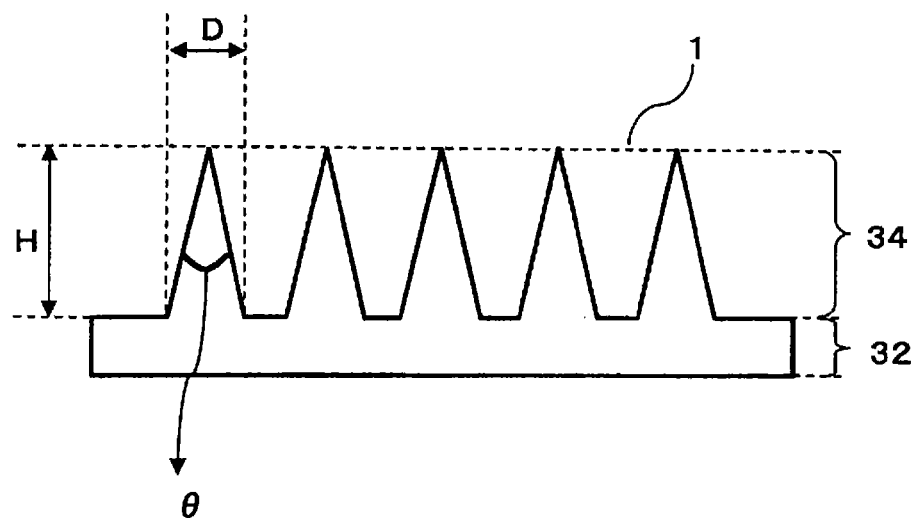
FIG. 2(b) is a cross-sectional view taken along an I-I' surface of the needle-shaped body in FIG. 2(a).

FIG. 1 is a perspective view of the needle-shaped body according to one embodiment of the invention. FIG. 2(a)-2(b) are a schematic top view and a schematic cross-sectional view of the needle-shaped body. Note that the needle-shaped body is characterized by including the at least two layers of the projection side layer and the support base side layer; however, neither the projection side layer nor the support base side layer is shown in the needle-shaped body shown in FIG. 1 and FIG. 2(a)-2(b).

The needle-shaped body represents a molded body that is formed of a support base 32 and a projection 34. A shape of the projection only needs to be a shape that is suitable to puncture the skin, and can appropriately be designed. More specifically, the shape of the projection may be a circular cone, a pyramid, a cylinder, a prism, a pencil shape (with a cylinder-shaped body and a conical-shaped tip), or the like. In addition, either (1) a shape with the one projection on the support base, or (2) a shape with the plural projections erected on the support base can be adopted.

In addition, when the plural projections are erected on the support base, the each projection is preferably arranged in an array. Here, the "array" indicates a state that the needle-shaped unit body is arranged, and includes patterns such as lattice arrangement, close packing arrangement, concentric arrangement, and random arrangement, for example.

FIG. 2(a) is a top view from the projection side of the needle-shaped body, and FIG. 2(b) is a cross-sectional view taken along an I-I' surface of the needle-shaped body in FIG. 2(a).

In a needle-shaped body 1, dimensions of the needle-shaped projection 34 preferably have thinness and a length that are suitable for forming a puncture hole in the skin. More specifically, a height H of the projection 34 shown in FIG. 2(b) is preferably within a range from 10 µm to 1,000 µm inclusive. The height H of the projection is a distance from the support base 32 to a tip of the projection 34.

The height H of the projection is preferably determined in consideration of how deep the puncture hole, which is formed when the needle-shaped body punctures within the above range, is formed in the skin.

Particularly, when the puncture hole, which is formed when the needle-shaped body punctures, is retained in "a horny layer", the height H of the projection of the needle-shaped body desirably falls within a range of 10 µm to 300 µm inclusive, for example, and more preferably, of 30 µm to 200 µm inclusive.

In addition, when the puncture hole, which is formed when the needle-shaped body punctures, is retained "in a length that penetrates the horny layer but does not reach a neural layer", the height H of the projection of the needle-shaped body desirably falls within a range of 200 µm to 700 µm inclusive, more preferably, of 200 µm to 500 µm inclusive, and further preferably, of 200 µm to 300 µm inclusive.

Furthermore, when the puncture hole, which is formed when the needle-shaped body punctures, has a "length that allows the puncture hole to reach a corium", the height H of the projection of the needle-shaped body preferably falls within a range of 200 µm to 500 µm inclusive. Moreover, when the puncture hole, which is formed when the needle-shaped body punctures, has a "length that allows the puncture hole to reach epidermis", the height H of the projection of the needle-shaped body preferably falls within a range of 200 µm to 300 µm inclusive.

A width D of the projection preferably falls within a range of 1 µm to 300 µm inclusive. The width D of the projection is preferably determined in consideration of how deep the puncture hole, which is formed when the needle-shaped body punctures within the above range, is formed in the skin, or the like.

The width D of the projection is a maximum length of a length of the projection that is in contact with the support base when the projection is projected in parallel with a base surface. For example, when the projection is in a shape of the circular cone, a diameter of a circle on a surface on which the projection and the support base contact each other corresponds to the width D. When the projection is in a shape of a square pyramid, a diagonal line of a square on the surface on which the projection and the support base contact each other corresponds to the width D. In addition, when the projection is in a shape of the cylinder, a diameter of a circle on a surface on which the projection and the support base contact each other corresponds to the width D. When the projection is in a shape of a square prism, a diagonal line of a square on the surface on which the projection and the support base contact each other corresponds to the width D.

An aspect ratio preferably falls within a range from 1 to 10 inclusive. An aspect ratio A is defined by using the height H and the width D of the projection as $A=H/D$.

In the needle-shaped body according to the embodiment, when the projection has a tip angle as in a conical shape and penetrates the horny layer, a tip angle $\theta$ of the projection desirably falls within a range from 5° to 30° inclusive, and more preferably, of 10° to 20° inclusive. Noted that the tip angle $\theta$ represents the maximum angle of angles (apex angles) when the projection is projected in parallel with the support base surface.

FIG. 3(a)-3(d) are schematic cross-sectional views of needle-shaped bodies. The needle-shaped bodies are characterized by including the at least two layers of the projection side layer and the support base side layer and in that the projection side layer and the support base side layer are formed of different constituents.

Figure 3A:
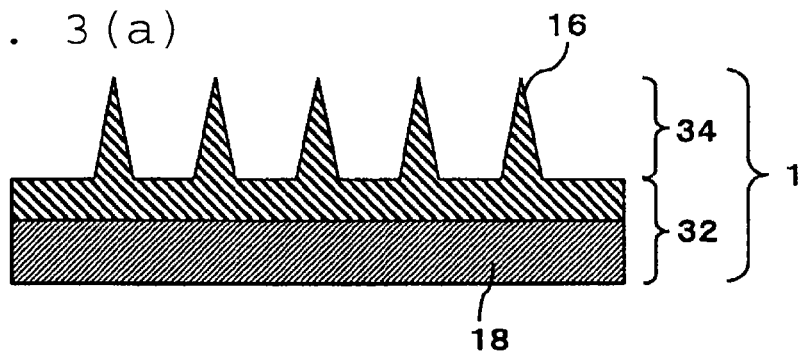
FIG. 3(a)-3(d) are schematic cross-sectional views of the needle-shaped body according to one embodiment of the invention.

In the needle-shaped body illustrated in FIG. 3(a), a projection side layer 16 and a support base side layer 18 are separated from each other in the support base 32.

Figure 3B:
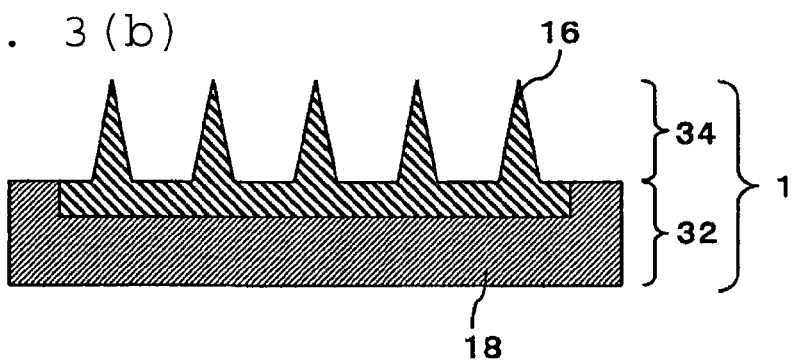

In the needle-shaped body illustrated in FIG. 3(b), the projection side layer 16 and the support base side layer 18 are separated from each other in the support base 32, and the projection side layer 16 in the support base 32 is further formed to have a smaller area than an outer shape of the support base.

Figure 3C:
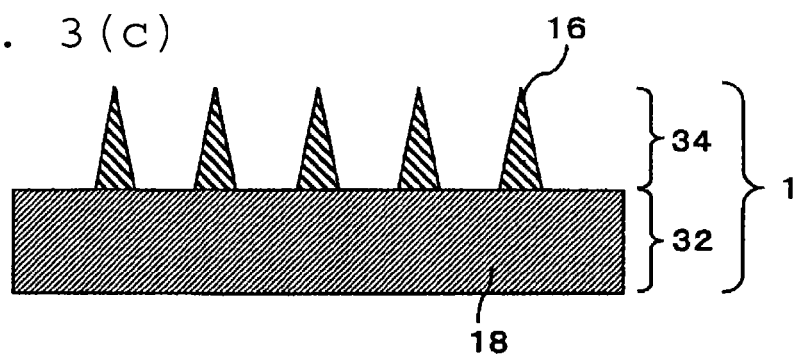

In the needle-shaped body illustrated in FIG. 3(c), the projection side layer 16 and the support base side layer 18 are separated from each other at a joined position of the support base 32 and the projection 34.

Figure 3D:
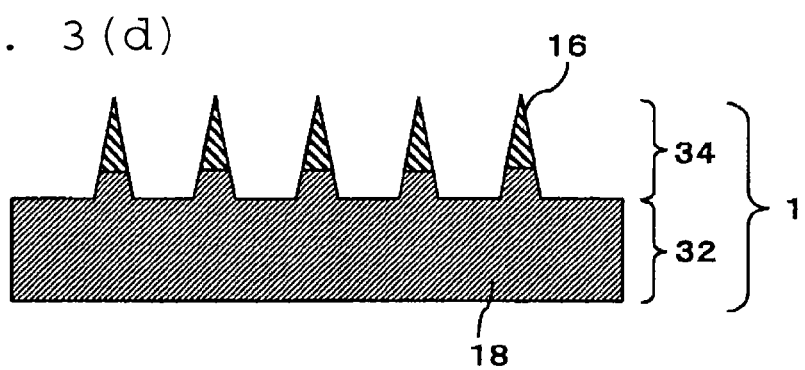
Figure 4A:
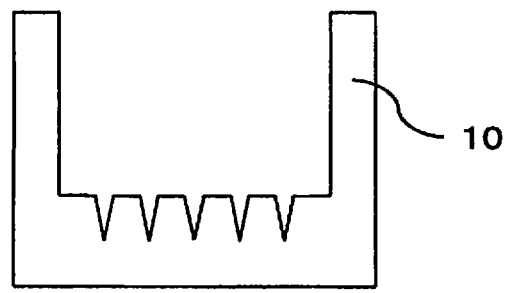
FIG. 4(a)-4(d) illustrate a method for manufacturing a needle-shaped body according to one embodiment of the invention, and illustrate a method for manufacturing when a needle-shaped body shown in FIG. 3(a) is manufactured.
Figure 4B:
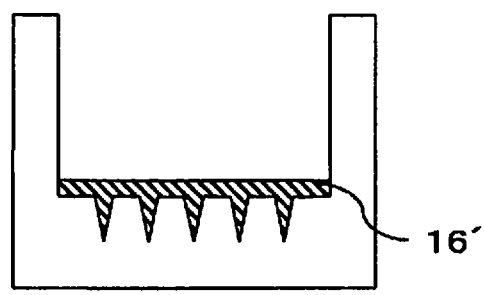
Figure 4C:
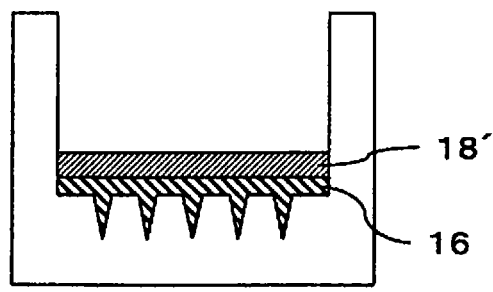
Figure 4D:
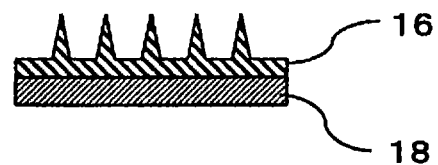
Figure 5A:
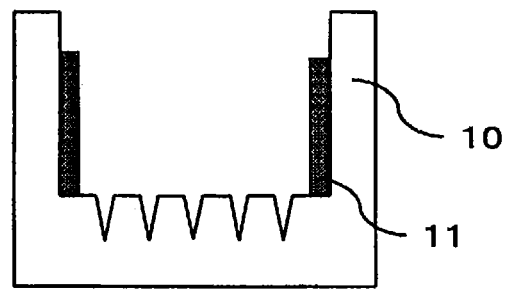
FIG. 5(a)-5(d) illustrate a method for manufacturing a needle-shaped body according to one embodiment of the invention, and illustrate a method for manufacturing when a needle-shaped body shown in FIG. 3(b) is manufactured.
Figure 5B:
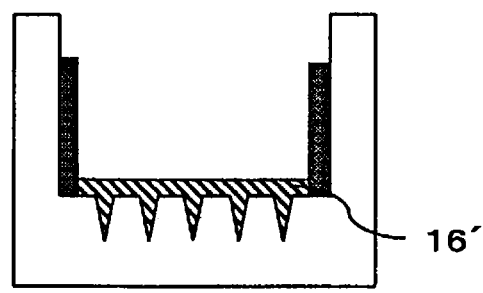
Figure 5C:
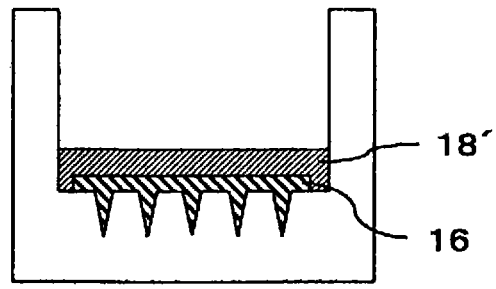
Figure 5D:
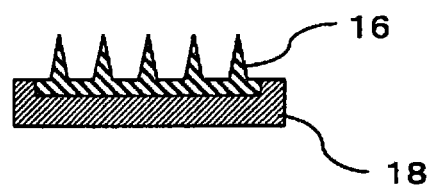

In the needle-shaped body illustrated in FIG. 3(d), the projection side layer 16 and the support base side layer 18 are separated from each other in the projection 34.

The needle-shaped body is characterized that the peeling strength between the projection side layer 16 and the support base side layer 18 is 8 N/15 mm in width or lower, the peeling strength being measured by following Japanese Industrial Standards JIS K6854-1 (1999) "Adhesives—Peel test for a flexible-bonded-to-rigid test specimen assembly—Part 1: 90° peel". The peeling strength between the projection side layer and the support base side layer is set to 8 N/15 mm in width or lower, so that both of the layers can easily be peeled. Accordingly, after the needle-shaped body punctures the skin, only the support base side layer can be peeled from the skin in a state that the projection side layer is in contact with the skin. Thus, the needle-shaped body that punctures the skin cannot easily be recognized. Therefore, a problem in appearance during use can be improved. Especially, the needle-shaped bodies in FIGS. 3(b), (c), (d) can each have profound, inventive effects.

Furthermore, in the needle-shaped body, the peeling strength between the projection side layer 16 and the support base side layer 18 is preferably from 0.5 N/15 mm in width to 8 N/15 mm in width inclusive. When the peeling strength is lower than 0.5 N/15 mm in width, the needle-shaped body may not be favorably peeled from the intaglio plate. More preferably, the peeling strength between the projection side layer 16 and the support base side layer 18 is from 1 N/15 mm in width to 3 N/15 mm in width inclusive.

In the needle-shaped body, a material for constituting the projection side layer 16 is desirably any of biodegradable polysaccharides, which include, for example, dextran, dextrin, pectin, pullulan, chondroitin sulfate, alginate, chitosan, carboxymethyl cellulose, hydroxymethyl cellulose, hydroxyethyl cellulose, hydroxypropyl cellulose, methyl cellulose, ethyl cellulose, and the like. In addition, the material may be a mixture of these biodegradable polysaccharides. Since the biodegradable polysaccharide is used as the projection side layer 16, the projection side layer 16 can be dissolved in the skin after the needle-shaped body punctures the skin. Thus, when the projection side layer contains a medicinal property, the delivery agent can promptly be introduced into the skin.

A material for constituting the support base side layer 18 is desirably a material that is a polysaccharide and has flexibility, and examples thereof include dextran, dextrin, pectin, pullulan, chondroitin sulfate, alginate, chitosan, carboxymethyl cellulose, hydroxymethyl cellulose, hydroxyethyl cellulose, hydroxypropyl cellulose, methyl cellulose, ethyl cellulose, and the like. In addition, the material may be a mixture of these biodegradable polysaccharides.

Among them, it is preferable to use pullulan and/or dextran as the material for constituting the projection side layer 16 and to use a material selected from hydroxypropyl cellulose, hydroxyethyl cellulose, methyl cellulose, hydroxypropyl methylcellulose as the material for constituting the support base side layer 18. The reason is because the peeling strength between the projection side layer and the support base side layer can easily be set to 8 N/15 mm in width or lower. This is because a combination of aqueous solutions of the materials becomes the liquid-liquid dispersion system and also because the aqueous solution of the material for constituting the projection side layer 16 has the greater specific gravity than the aqueous solution of the material for constituting the support base side layer 18.

The needle-shaped body can contain the delivery agent to be delivered into the skin. As the delivery agent, a pharmacologically active substance or a cosmetic delivery agent can be contained. At this time, when a material with a fragrance is used as the delivery agent, the aroma can be applied upon use, and thus can preferably be used as a beauty product.

The pharmacologically active substance can appropriately be selected according to its application. For example, the pharmacologically active substance may be a vaccine for influenza or the like, a medicine suitable as a painkiller for cancer patients, insulin, a biopharmaceutical, a gene therapy medicine, an injection, an oral medicine, a preparation for application to the skin, or the like. Since the needle-shaped body punctures the skin, in addition to the pharmacologically active substance that is used for the conventional transdermal administration, the needle-shaped body can be applied for the pharmacologically active substance that requires a subcutaneous injection. Particularly, as for the vaccine as the injection and the like, since there is no pain during administration when the needle-shaped body is used, use of the needle-shaped body is suitable for children. In addition, as for conventional administration of the oral medicine, a child has a difficulty in swallowing the oral medicine. Since there is no need to swallow the medicine during administration when the needle-shaped body is used, the use of the needle-shaped body is suitable for children.

In the needle-shaped body of the dissolved type in which a needle that has punctured is eluted in the skin and delivers the delivery agent in the body, the delivery agent is contained in the needle-shaped body. However, there has been a problem that a medicine that is not eluted in the skin but remains in the support base of the needle-shaped body is wasted. A waste of the medicine can be solved by containing the delivery agent only in the projection side layer.

The cosmetic delivery is a composition used as a cosmetic product and the beauty product. For example, a moisturizer, a colorant, a perfume, a physiologically active substance that shows a beauty effect (an improvement effect on wrinkles, blemishes, stretch marks, or the like, an improvement effect on hair loss, or the like) or the like can be raised.

In addition, particularly, when a depth of the puncture hole is retained "in the horny layer", the delivery agent can be retained in the horny layer. Since the horny layer is constantly and newly produced due to metabolism, the delivery agent in the horny layer is eliminated from the body over time. Thus, the delivery agent can be eliminated by cleansing the skin, peeling the skin, or the like.

Furthermore, when the puncture hole is retained in "the length that penetrates the horny layer but does not reach the neural layer", the delivery agent can be delivered to a position deeper than the horny layer. Since the puncture hole formed in the horny layer is mended over time, the delivery agent that is delivered under the horny layer is retained in a living body in a state of being barriered against the outside by the horny layer. Accordingly, the delivery agent can be retained for a long time period since an opportunity of the peeling thereof due to metabolism of the horny layer or cleansing in the skin care can be reduced.

Thus, when the delivery agent used for beauty application, a long-term cosmetic condition can be maintained. Therefore, the needle-shaped body can favorably be used to deliver the cosmetic delivery agent to a portion where long-term retention of a color is desired, particularly, eyebrows, areas around eyes, an area around lips, or the like.

Moreover, the needle-shaped body can favorably be used for a medical direction (makeup, a treatment, or the like) for abnormality of the skin (spotted rash or the like) that is caused by a portion under the horny layer.

The needle-shaped body is characterized in that the projection side layer and the support base side layer are formed of different constituents. "(Being) formed of different constituents" indicates that polysaccharides used for the projection side layer and the support base side layer may be different materials or that the same polysaccharide is used for the projection side layer and the support base side layer but other constituents such as the delivery agents may be different materials.

Noted that, of the needle-shaped body, a needle-shaped body in which the projection side layer and the support base side layer are not clearly separated and that includes a mixed layer of the projection side layer and the support base side layer between the projection side layer and the support base side layer is not excluded. In the needle-shaped body that includes the mixed layer of the projection side layer and the support base side layer, the peeling strength between the projection side layer and the support base side layer, which will be described below, can be increased.

The needle-shaped body can be adopted such that the delivery agent is contained only in the projection side layer and thus is not contained in the support base side layer. The delivery agent can efficiently be used by containing the delivery agent only in the projection side layer.

Meanwhile, when the delivery agent is administered by using the needle-shaped body, the delivery agent may be applied onto the skin as a subject either before the needle-shaped body punctures the skin or after the needle-shaped body punctures the skin. At this time, the delivery agent may also be arranged in the needle-shaped body, and the delivery agent may be applied to the skin surface as the subject.

In addition, the needle-shaped body may include the delivery agent on a surface of the projection.

Furthermore, in the needle-shaped body, the support base may have flexibility. Since the support base has the flexibility, the needle-shaped body can favorably puncture the subject with flexibility such as a curved surface or the skin of the living body. When having the flexibility, the support base is formed in a rolled shape. Accordingly, a roller with the erected projection can be formed.

For the medical direction with use of the needle-shaped body, an applicator for fixing a position and a direction of insertion may be used.

Next, a method for manufacturing the needle-shaped body will be described.

FIG. 4(a)-4(d) illustrate a method for manufacturing a needle-shaped body. FIG. 4(a)-4(d) illustrate a method for manufacturing when the needle-shaped body shown in FIG. 3(a) is manufactured.

<A Process of Preparing the Aqueous Solutions>

The aqueous solutions of the materials that form the projection side layer 16 and the support base side layer 18 are each prepared.

<A Process of Producing the Intaglio Plate>

Next, an intaglio plate 10 with a needle pattern is prepared (FIG. 4(*a*)). As a method for manufacturing an original plate that determines a shape of the needle-shaped body, a known method for manufacturing can appropriately be used in accordance with the shape of the needle-shaped body. At this time, a technique of microfabrication may be used to form the original plate, and as the technique of microfabrication, for example, a lithography method, a wet etching method, a dry etching method, a sandblast method, a laser machining method, a precision machining method, or the like may be used. As a method for forming the intaglio plate from the original plate, a known shape transfer method may appropriately be used. For example, (1) forming the intaglio plate of Ni by a Ni electroforming method, (2) transfer molding by using a molten resin, or the like can be raised.

<A Process of Filling a Material of the Needle-Shaped Body>

Next, as shown in FIG. 4(*b*), the intaglio plate 10 is supplied with an aqueous solution 16' of a material that forms the projection side layer. A solvent for the aqueous solution 16' of the material that forms the projection side layer only needs to be a solvent that dissolves the material of the needle-shaped body, and water is used therefor. Noted that another constituent of the solvent, such as alcohol, may be added to water.

After the aqueous solution is supplied, heat drying may be performed in some cases. It is possible by performing the heat drying to suppress mixture in the vicinity of an interface with an aqueous solution 18' of a material that forms the support base side layer and is filled next. Especially when the aqueous solution 18' of the material that forms the support base side layer has the greater specific gravity than the aqueous solution 16' of the material that forms the projection side layer, the heat drying should be performed.

Next, as shown in FIG. 4(*c*), the aqueous solution 18' of the material that forms the support base side layer is supplied on top of the projection side layer 16. A solvent for the aqueous solution 18' of the material that forms the support base side layer only needs to be a solvent that dissolves the material of the needle-shaped body, and water is used therefor. Noted that another constituent of the solvent, such as alcohol, may be added to water. Particularly, it is desirable that the aqueous solution 16' of the material that forms the projection side layer and the aqueous solution 18' of the material that forms the support base side layer are the liquid-liquid dispersion system in which the aqueous solution 16' and the aqueous solution 18' are not mixed with each other. In addition, the aqueous solution 16' of the material that forms the projection side layer desirably has the greater specific gravity than the aqueous solution 18' of the material that forms the support base side layer.

For example, the aqueous solution 16' of the material that forms the projection side layer and the aqueous solution 18' of the material that forms the support base side layer are the liquid-liquid dispersion system in which the aqueous solution 16' and the aqueous solution 18' are not mixed with each other, and the aqueous solution 16' of the material that forms the projection side layer can have the greater specific gravity than the aqueous solution 18' of the material that forms the support base side layer. On the premise of the above, it is possible to select a combination of the aqueous solution 16' of the material that forms the projection side layer and the aqueous solution 18' of the material that forms the support base side layer, the aqueous solution 16' being selected from a pullulan solution and a dextran solution and the aqueous solution 18' being selected from a hydroxypropyl cellulose solution, a hydroxyethyl cellulose solution, a methyl cellulose solution, and a hydroxypropyl methylcellulose solution.

For a method for supplying the aqueous solution, a known method may appropriately be selected in accordance with a shape and dimensions of the intaglio plate. For example, as the method for supplying the aqueous solution, a spin coating method, an ink jet method, a method for using a dispenser, a casting method, or the like may be used. In addition, upon filling, an environment around the intaglio plate may be placed under reduced pressure or under vacuum.

<A Process of Drying the Material of the Needle-Shaped Body>

Next, the aqueous solution 18' of the material that forms the support base side layer is dried and hardened. A drying method may appropriately be selected in accordance with the environment, such as natural drying, bottom surface heating with a hot plate, and drying by hot air drying. Noted that a drying needs to be performed at a temperature at which the aqueous solution is not boiled. The drying temperature is preferably performed at the temperature that is at least 110° C. or lower.

<A Process of Peeling the Needle-Shaped Body from the Intaglio Plate>

The needle-shaped body 1 can be obtained when being peeled from the intaglio plate 10 after completion of drying. Since the aqueous solution 16' of the material that forms the projection side layer and the aqueous solution 18' of the material that forms the support base side layer form the liquid-liquid dispersion system in which the aqueous solution 16' and the aqueous solution 18' are not mixed with each other, the aqueous solution 16' of the material that forms the projection side layer and the aqueous solution 18' of the material that forms the support base side layer are dried while keeping a double-layered state. Thus, the needle-shaped body having a double-layered structure can be obtained.

FIG. 5(*a*)-5(*d*) illustrate a method for manufacturing a needle-shaped body. FIG. 5(*a*)-5(*d*) illustrate a method for manufacturing when the needle-shaped body shown in FIG. 3(*b*) is manufactured.

In FIG. 5(*a*)-5(*d*), when the intaglio plate 10 with the needle pattern is prepared (FIG. 5(*a*)), a second plate 11 is prepared that is detachable and can surround an outer edge of a portion of the intaglio plate, the portion corresponding to the support base.

Next, as shown in FIG. 5(*b*), the aqueous solution 16' of the material that forms the projection side layer is supplied to the intaglio plate 10. Then, the aqueous solution in the intaglio plate is dried. The heat drying is preferred as drying, and it is possible by performing drying to suppress the mixture in the vicinity of the interface with the aqueous solution 18' of the material that forms the support base side layer and is filled next. Next, the second plate 11 is detached from the intaglio plate. After the removal of the second plate from the intaglio plate, as shown in FIG. 5(*c*), the aqueous solution 18' of the material that forms the support base side layer is supplied on the top of the projection side layer 16. Then, the aqueous solution 18' of the material that forms the support base side layer is dried and hardened. The needle-shaped body shown in FIG. 5(*d*) is obtained when being peeled from the intaglio plate 10 after the completion of drying.

FIG. 6(a)-6(d) illustrate a method for manufacturing a needle-shaped body. FIG. 6(a)-6(d) illustrates the method for manufacturing when the needle-shaped body shown in FIG. 3(d) is manufactured.

Figure 6A:
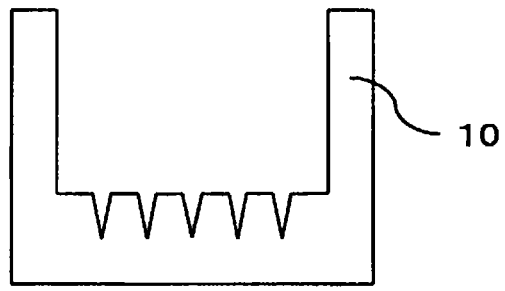
FIG. 6(a)-6(d) illustrate a method for manufacturing a needle-shaped body according to one embodiment of the invention, and illustrate a method for manufacturing when a needle-shaped body shown in FIG. 3(d) is manufactured.
Figure 6B:
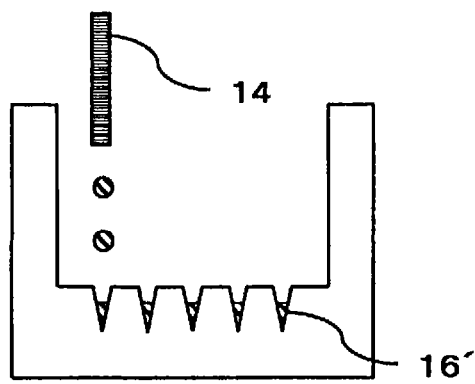
Figure 6C:
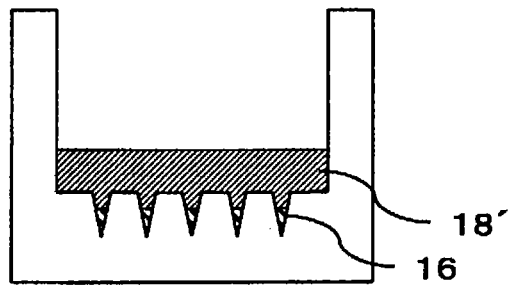
Figure 6D:
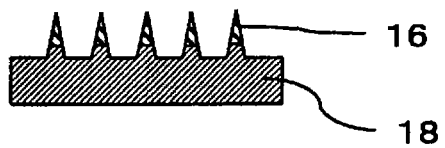

In FIG. 6(a), the intaglio plate 10 with the needle pattern is prepared. Next, as shown in FIG. 6(b), the aqueous solution 16' of the material that forms the projection side layer is supplied to the intaglio plate 10. At this time, the aqueous solution 16' of the material that forms the projection side layer is supplied by the ink jet method to a portion of the intaglio plate that corresponds to the projection. In FIG. 6(b), the aqueous solution 16' of the material that forms the projection side layer is discharged from an ink jet nozzle 14. Then, the aqueous solution in the intaglio plate is dried. The heat drying is preferred as drying, and it is possible by performing drying to suppress the mixture in the vicinity of the interface with the aqueous solution 18' of the material that forms the support base side layer and is filled next. Next, as shown in FIG. 6(c), the aqueous solution 18' of the material that forms the support base side layer is supplied on the top of the projection side layer 16. Then, the aqueous solution 18' of the material that forms the support base side layer is dried and hardened. The needle-shaped body shown in FIG. 6(d) is obtained when being peeled from the intaglio plate 10 after the completion of drying.

When the needle-shaped body in which only the projection includes the projection side layer is manufactured as shown in FIGS. 3(c), (d), the ink jet method can favorably be used as a means for supplying the aqueous solution 16' of the material that forms the projection side layer to the intaglio plate 10. It is possible by using the ink jet method to significantly reduce usage of the expensive delivery agent.

Next, a method for puncturing the skin with the needle-shaped body according to one embodiment of the invention will be described.

Figure 7A:
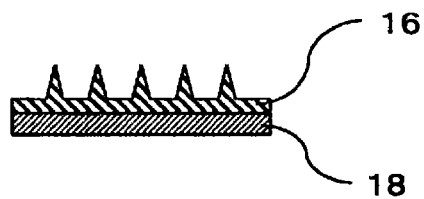
FIG. 7(a)-7(c) illustrate a method for puncturing a skin with the needle-shaped body according to one embodiment of the invention.
Figure 7B:
Figure 7C:
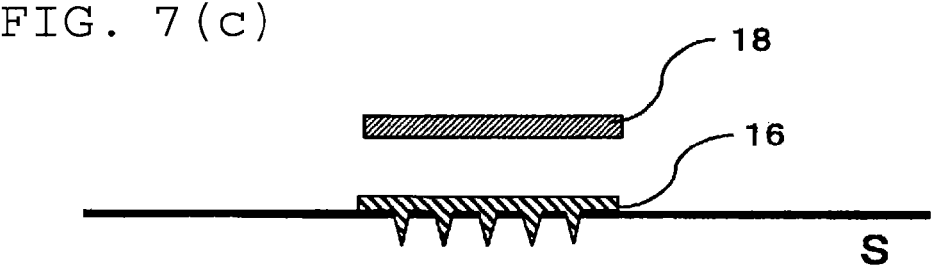

FIG. 7(a)-7(c) illustrate a method for puncturing the skin with the needle-shaped body.

First, the needle-shaped body that includes the projection side layer 16 and the support base side layer 18 is prepared (FIG. 7(a)). Next, the needle-shaped body punctures a skin S (FIG. 7(b)). Finally, the needle-shaped body is peeled at the interface between the projection side layer 16 and the support base side layer 18 (FIG. 7(c)). As described above, in the needle-shaped body, the projection side layer and the support base side layer can easily be peeled. Accordingly, after the needle-shaped body punctures the skin, only the support base side layer can be peeled from the skin in the state that the projection side layer is in contact with the skin. Thus, the needle-shaped body that punctures the skin cannot easily be recognized.

Figure 8A:
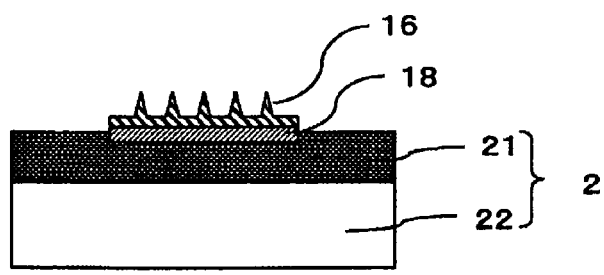
FIG. 8(a)-8(c) illustrate a method for puncturing the skin with the needle-shaped body according to another embodiment of the invention.
Figure 8B:
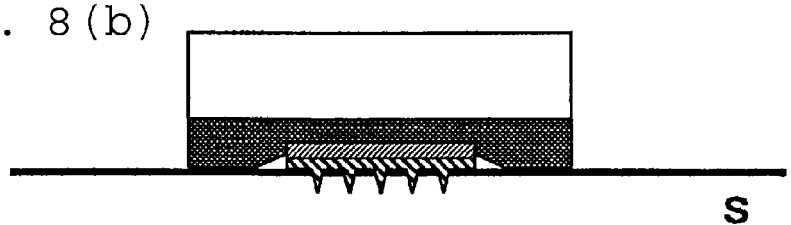
Figure 8C:
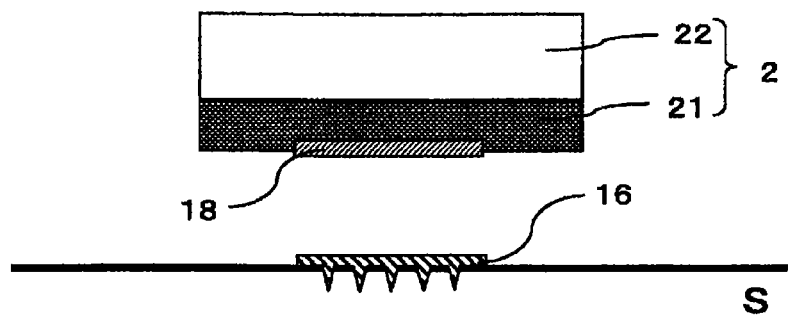

FIG. 8(a)-8(c) illustrate a method for puncturing the skin with a needle-shaped body according to another embodiment of the invention.

First, an adhesive tape 2 is adhered to the support base side of the needle-shaped body that includes the projection side layer 16 and the support base side layer 18. The adhesive tape 2 includes an adhesive layer 21 on top of a base 22 (FIG. 8(a)). Next, the needle-shaped body that is fixed to the adhesive tape 2 punctures the skin S (FIG. 8(b)). Finally, the needle-shaped body is peeled at the interface between the projection side layer 16 and the support base side layer 18 (FIG. 8(c)).

Noted that, in the method for puncturing the skin by using the needle-shaped body of the invention, after the needle-shaped body punctures the skin S (FIG. 8(b)), the needle-shaped body can be adhered to the skin and retained so by the adhesive layer of the adhesive tape in a state that the needle-shaped body punctures the skin, and then the needle-shaped body can be peeled at the interface between the projection side layer 16 and the support base side layer 18 (FIG. 8(c)).

EXAMPLES

The invention will hereinafter be described in detail by using examples and comparative examples; however, the invention is not limited to these embodiments.

Example 1

The needle-shaped body shown in FIG. 3(a) was produced by the following method.

(1) First, an original plate of the needle-shaped body was formed by using precision machining, the original plate having 36 square pyramids (a bottom surface of 38 µm×38 µm, a height of 120 µm) arranged in a lattice pattern of six rows and six columns at 1 mm intervals on a silicon base. Next, a nickel film of 500 µm in thickness is formed by plating on the original plate of the needle-shaped body, which is formed of the silicon base. Wet etching is performed to remove the silicon base by a potassium hydroxide solution of 30 wt % concentration that is heated to 90° C., so as to produce an intaglio plate formed of nickel.

(2) A pullulan (Tokyo Chemical Industry Co., Ltd.) solution of 10 wt. % and a hydroxypropyl cellulose (Tokyo Chemical Industry Co., Ltd.) solution of 10 wt. % were prepared.

(3) The spin coating method was used to fill the produced intaglio plate with the pullulan solution.

(4) The intaglio plate filled in with the pullulan solution was placed on a hot plate set at 90° C. and dried for 30 minutes to evaporate moisture.

(5) The spin coating method was used to apply the hydroxypropyl cellulose solution onto the intaglio plate, in which a layer formed of pullulan was formed.

(6) The intaglio plate was dried at a room temperature to form the needle-shaped body.

(7) The needle-shaped body was peeled from the intaglio plate.

Example 2

The needle-shaped body shown in FIG. 3(a) is produced by the following method.

(1) First, the intaglio plate that is formed of nickel and is the same as Example 1 was produced.

(2) The pullulan (Tokyo Chemical Industry Co., Ltd.) solution of 10 wt. % and a methyl cellulose (Tokyo Chemical Industry Co., Ltd.) solution of 1 wt. % were prepared.

(3) The spin coating method was used to fill the produced intaglio plate with the pullulan solution.

(4) The intaglio plate filled in with the pullulan solution was placed on the hot plate set at 90° C. and dried for 30 minutes to evaporate the moisture.

(5) The spin coating method was used to apply the methyl cellulose solution onto the intaglio plate, in which the layer formed of pullulan was formed.

(6) The intaglio plate was dried at the room temperature to form the needle-shaped body.

(7) The needle-shaped body was peeled from the intaglio plate.

Example 3

The needle-shaped body shown in FIG. 3(a) is produced by the following method.

(1) First, the intaglio plate that is formed of nickel and is the same as Example 1 was produced.

(2) The pullulan (Tokyo Chemical Industry Co., Ltd.) solution of 10 wt. % and a hydroxyethyl cellulose (Tokyo Chemical Industry Co., Ltd.) solution of 10 wt. % were prepared.

(3) The ink jet method was used to fill the produced intaglio plate with the pullulan solution.

(4) The intaglio plate filled in with the pullulan solution was placed on the hot plate set at 90° C. and dried for 30 minutes to evaporate the moisture.

(5) The spin coating method was used to apply the hydroxyethyl cellulose solution onto the intaglio plate, in which the layer formed of pullulan was formed.

(6) The intaglio plate was dried at the room temperature to form the needle-shaped body.

(7) The needle-shaped body was peeled from the intaglio plate.

Example 4

The needle-shaped body shown in FIG. 3(a) is produced by the following method.

(1) First, the intaglio plate that is formed of nickel and is the same as Example 1 was produced.

(2) The pullulan (Tokyo Chemical Industry Co., Ltd.) solution of 10 wt. % and a hydroxypropyl cellulose (Tokyo Chemical Industry Co., Ltd.) solution of 10 wt. % were prepared.

(3) The spin coating method was used to fill the produced intaglio plate with the pullulan solution.

(4) The spin coating method was used to apply the hydroxypropyl cellulose solution onto the intaglio plate, which was filled in with the pullulan solution, without drying the pullulan solution filled in the intaglio plate.

(5) The intaglio plate was dried at the room temperature.

(6) The needle-shaped body was peeled from the intaglio plate of (5).

Example 5

The needle-shaped body shown in FIG. 3(a) is produced by the following method.

(1) First, the intaglio plate that is formed of nickel and is the same as Example 1 was produced.

(2) A dextran (Tokyo Chemical Industry Co., Ltd.) solution of 10 wt. % and the hydroxypropyl cellulose (Tokyo Chemical Industry Co., Ltd.) solution of 10 wt. % were prepared.

(3) The spin coating method was used to fill the produced intaglio plate with the dextran solution.

(4) The spin coating method was used to apply the hydroxypropyl cellulose solution onto the intaglio plate, which was filled in with the dextran solution, without drying the dextran solution filled in the intaglio plate.

(5) The intaglio plate was dried at the room temperature.

(6) The needle-shaped body was peeled from the intaglio plate of (5).

Comparative Example 1

The needle-shaped body is produced by the following method.

(1) First, the intaglio plate that is formed of nickel and is the same as Example 1 was produced.

(2) The hydroxypropyl cellulose (Tokyo Chemical Industry Co., Ltd.) solution of 10 wt. % was prepared.

(3) The spin coating method was used to fill the produced intaglio plate with the hydroxypropyl cellulose solution.

(4) The intaglio plate filled in with the hydroxypropyl cellulose solution was placed on the hot plate set at 90° C. and dried for 30 minutes to evaporate the moisture.

(5) The spin coating method was used to apply the hydroxypropyl cellulose solution onto the intaglio plate, in which a layer formed of hydroxypropyl cellulose was formed.

(6) The intaglio plate was dried at the room temperature to form the needle-shaped body.

(7) The needle-shaped body was peeled from the intaglio plate.

Comparative Example 2

The needle-shaped body is produced by the following method.

(1) First, the intaglio plate that is formed of nickel and is the same as Example 1 was produced.

(2) The pullulan (Tokyo Chemical Industry Co., Ltd.) solution of 10 wt. % was prepared.

(3) The spin coating method was used to fill the produced intaglio plate with the pullulan solution.

(4) The intaglio plate filled in with the pullulan solution was placed on the hot plate set at 90° C. and dried for 30 minutes to evaporate the moisture.

(5) The spin coating method was used to apply the pullulan solution onto the intaglio plate, in which the layer formed of pullulan was formed.

(6) The intaglio plate was dried at the room temperature to form the needle-shaped body.

(7) The needle-shaped body was peeled from the intaglio plate.

Comparative Example 3

The needle-shaped body is produced by the following method.

(1) First, the intaglio plate that is formed of nickel and is the same as Example 1 was produced.

(2) The pullulan (Tokyo Chemical Industry Co., Ltd.) solution of 10 wt. % and a sodium alginate (Tokyo Chemical Industry Co., Ltd.) solution of 10 wt. % were prepared.

(3) The spin coating method was used to fill the produced intaglio plate with the pullulan solution.

(4) The intaglio plate filled in with the pullulan solution was placed on the hot plate set at 90° C. and dried for 30 minutes to evaporate the moisture.

(5) The spin coating method was used to apply the sodium alginate solution onto the intaglio plate, in which the layer formed of pullulan was formed.

(6) The intaglio plate was dried at the room temperature to form the needle-shaped body.

(7) The needle-shaped body was peeled from the intaglio plate.

(Result)

<Confirmation of the Liquid-Liquid Dispersion System and the Specific Gravity>

The two aqueous solutions that were used in the methods of manufacturing a needle-shaped body in Example 1 to Example 5 and Comparative Example 1 to Comparative Example 3 were poured into a beaker and left for five minutes, and states of the aqueous solutions in the beaker were confirmed. Regarding the aqueous solutions in Examples 1 to 5, a condition (an interface) that each of the aqueous solutions was separated in an upper part or a lower part in the beaker was confirmed, and each of the aqueous solutions was confirmed to be the liquid-liquid dispersion system. On the other hand, regarding the aqueous solutions in Comparative Examples 1 to 3, the condition (the interface) of separation in the upper part and the lower part was not confirmed.

In addition, regarding the aqueous solutions in Examples 1 to 5, it was confirmed that the pullulan solution or the dextran solution existed in the lower part of the beaker and that the hydroxypropyl cellulose solution, the methyl cellulose solution, or the hydroxyethyl cellulose solution existed in the upper part of the beaker, and that the pullulan solution or the dextran solution had the greater specific gravity than the hydroxypropyl cellulose solution, the methyl cellulose solution, or the hydroxyethyl cellulose solution.

<Comparison of the Needle-Shaped Body Structures>

Each of the needle-shaped bodies of Example 1 to Example 5 and Comparative Example 1 to Comparative Example 3 was cut perpendicular to the support base, and a cross section thereof was observed with a scanning electron microscope. Each of Examples 1 to 5 had the double-layered structure. It was observed in Comparative Example 3 that sodium alginate and pullulan were mixed at the interface between the projection side layer and the support base side layer. Although the double-layered structure was confirmed in Example 4, it was observed that hydroxypropyl cellulose and pullulan were partially mixed at the interface between the projection side layer and the support base side layer. Each of Comparative Example 1 and Comparative Example 2 had a single-layered structure, and the interface was not observed therein.

<Measurement of 90 Degree Peeling Strength of the Needle-Shaped Bodies>

Adhesion strength between the projection side layer and the support base side layer was measured by referring to Japanese Industrial Standards JIS K6854-1 (1999) "Adhesives—Peel test for a flexible-bonded-to-rigid test specimen assembly—Part 1: 90° peel". The needle-shaped body, which was peeled from the intaglio plate, was sliced into a strip of 15 mm in width. A portion of the needle-shaped body sliced into the strip was peeled into the projection side layer and the support base side layer, and ends of the strip were fixed to a grasp portion of a tensile test machine. At this time, the ends were fixed for 90 degree peeling. A tensile test was performed from the above state at a grasp moving speed of 50 mm/min, and the maximum force was set to the peeling strength. Results of strength measurements of the needle-shaped bodies are shown in Table 1. Noted that bonding strength between the projection side layer and the support base side layer was so high in Comparative Example 1 and Comparative Example 2 that the projection side layer and the support base side layer could not be peeled at the interface therebetween.

TABLE 1

| | Constituent | | | Peeling strength |
|---|---|---|---|---|
| | Projection side layer | Support base side layer | Layer structure | [N/15 mm in width] |
| Example 1 | Pullulan | Hydroxypropyl cellulose | Double-layered | 0.9 |
| Example 2 | Pullulan | Methyl cellulose | Double-layered | 0.6 |
| Example 3 | Pullulan | Hydroxyethyl cellulose | Double-layered | 1.0 |
| Example 4 | Pullulan | Hydroxypropyl cellulose | Double-layered | 1.5 |
| Example 5 | Dextran | Hydroxypropyl cellulose | Double-layered | 0.7 |
| Comparative Example 1 | Hydroxypropyl cellulose | Hydroxypropyl cellulose | Single-layered | |
| Comparative Example 2 | Pullulan | Pullulan | Single-layered | |
| Comparative Example 3 | Pullulan | Sodium Alginate | Double-layered | 9.5 |

Since the aqueous solution on the projection side layer, which was filled in the intaglio plate, was dried in Example 1 to Example 3 and Example 5, the molded needle-shaped body obtained the double-layered structure in which the interface was clearly confirmed. In Example 4 in which the aqueous solution on the projection side layer was not dried after being filled, although the molded needle-shaped body obtained the double-layered structure, it was confirmed that the materials were partially mixed at the interface between the projection side layer and the support base side layer. The peeling strength between the two layers was slightly higher than that in Example 1 and required a force of 1.5 N/15 mm in width.

Meanwhile, in Comparative Example 3, since sodium alginate and pullulan were mixed at the interface between the projection side layer and the support base side layer, an adhesive force of the two layers was large, and a force of 9.5 N/15 mm in width was required.

In the field of transdermal administration, a method for perforating the skin by using a needle-shaped body that is formed with a needle of μm order and administering a medicine or the like into the skin has been suggested (see PTL 1).

In addition, as a method for manufacturing a needle-shaped body, it has been suggested to produce an original plate by machining, form a transfer plate from the original plate, and perform transfer molding by using the transfer plate (see PTL 2).

Furthermore, as the method for manufacturing a needle-shaped body, it has been suggested to produce the original plate by an etching method, form the transfer plate from the original plate, and perform the transfer molding by using the transfer plate (see PTL 3).

Moreover, as a material for constituting the needle-shaped body, a material is desired that does not cause a harmful effect on the human body even when the damaged needle-shaped body remains in the body. As such a material, a biocompatible material, such as chitin or chitosan, has been suggested (see PTL 4).

PTL 1: JP-A-48-93192
PTL 2: WO 2008/013282
PTL 3: WO 2008/004597
PTL 4: WO 2008/020632

When such a biocompatible material is used to produce the needle-shaped body, it is common to produce the needle-shaped body by removing a solvent from a solution of the material by a method such as drying. As for the needle-shaped body of a dissolved type, a needle portion of which contains the delivery agent and is dissolved in the skin after the skin is punctured with the needle-shaped body, the needle-shaped body needs to be adhered to the skin for a certain time period, which causes a problem in appearance. The problem has especially been serious when a face is punctured with the needle-shaped body.

The present invention addresses a problem by providing a method for manufacturing a needle-shaped body and a needle-shaped body to solve the problem.

In order to solve the above problem, the first aspect of the invention is a method for manufacturing a needle-shaped body that includes a needle-shaped projection and a support base for supporting the projection, the method for manufacturing a needle-shaped body characterized by including: a process of supplying an aqueous solution of a material forming a projection-side-layer to an intaglio plate that has a recess corresponding to the projection; a process of supplying an aqueous solution of a material forming a support-base-layer to the intaglio plate; a process of drying the aqueous solutions in the intaglio plate to form a needle-shaped body; and a process of peeling the needle-shaped body from the intaglio plate, in that the aqueous solution of the material forming a projection-side-layer and the aqueous solution of the material forming a support-base-side-layer are a liquid-liquid dispersion system.

The second aspect of the invention is the method for manufacturing a needle-shaped body of the first aspect, characterized in that peeling strength between a projection side layer and a support base side layer is 8 N/15 mm in width or lower.

The third aspect of the invention is the method for manufacturing a needle-shaped body of the first aspect, characterized by including a process of drying the aqueous solution of the material forming a projection-side-layer in the intaglio plate after the process of supplying the aqueous solution of the material forming a projection-side-layer to the intaglio plate and before the process of supplying the aqueous solution of the material forming a support-base-side-layer to the intaglio plate.

The fourth aspect of the invention is the method for manufacturing a needle-shaped body of the first aspect, characterized in that specific gravity of the aqueous solution of the material forming a projection-side-layer is greater than specific gravity of the aqueous solution of the material forming a support-base-side-layer.

The fifth aspect of the invention is the method for manufacturing a needle-shaped body of the first aspect, characterized in that the material forming a projection-side-layer contains a material selected from pullulan and dextran and the material forming a support-base-side-layer contains a material selected from hydroxypropyl cellulose, hydroxyethyl cellulose, methyl cellulose, and hydroxypropyl methyl cellulose.

The sixth aspect of the invention is a needle-shaped body that includes a needle-shaped projection and a support base for supporting the projection, the needle-shaped body characterized by including at least two layers of a projection side layer and a support base side layer, in that peeling strength between the projection side layer and the support base side layer is 8 N/15 mm in width or lower.

The seventh aspect of the invention is a needle-shaped body that includes a needle-shaped projection and a support base for supporting the projection, the needle-shaped body characterized by including at least two layers of a projection side layer and a support base side layer, in that a material forming a projection-side-layer contains a material selected from pullulan and dextran and a material forming a support-base-side-layer contains a material selected from hydroxy-propyl cellulose, hydroxyethyl cellulose, methyl cellulose, and hydroxypropyl methyl cellulose.

In the needle-shaped body of a double-layered structure that can be obtained by the method for manufacturing a needle-shaped body of the invention, the projection side layer and the support base side layer can easily be peeled. Accordingly, after the needle-shaped body punctures the skin, only the support base side layer can be peeled from the skin in a state that the projection side layer is in contact with the skin. Thus, the needle-shaped body that punctures the skin cannot easily be recognized.

INDUSTRIAL APPLICABILITY

The needle-shaped body according to an embodiment of the invention can be used in various fields where the fine needle-shaped body is needed. For example, the needle-shaped body can be expected in application in a MEMS device, an optical member, a sample jig, drug development, medical practice, the cosmetic product, the beauty application, and the like.

DESCRIPTION OF REFERENCE NUMERALS

1: needle-shaped body
34: projection
32: support base
16: projection side layer
18: support base side layer
10: intaglio plate
11: second plate
16': aqueous solution of a material that forms a projection side layer
18': aqueous solution of a material that forms a support base side layer
14: ink jet nozzle
2: adhesive tape
21: adhesive layer
22: base Obviously, numerous modifications and variations of the present invention are possible in light of the above teachings. It is therefore to be understood that within the scope of the appended claims, the invention may be practiced otherwise than as specifically described herein.

The invention claimed is:

1. A needle-shaped body, comprising:
a needle-shaped projection; and
a support base which supports the needle-shaped projection,
wherein at least a portion of the needle-shaped projection comprises a projection side layer, at least a portion of the support base comprises a support base side layer, the projection side layer is formed directly on the support base side layer, and the needle-shaped projection and the support base comprise different materials such that peeling strength between the projection side layer and the support base side layer is 8 N/15 mm in width or lower.

2. The needle-shaped body according to claim 1, wherein the support base side layer and a portion of the projection side layer form the support base.

3. The needle-shaped body according to claim 2, wherein the portion of the projection side layer in the support base has a smaller area than an outer shape of the support base.

4. The needle-shaped body according to claim 1, wherein the projection side layer and a portion of the support base side layer form the needle-shaped projection.

5. The needle-shaped body according to claim 1, wherein the projection side layer and the support base side layer are formed such that a boundary of the projection side layer and the support base side layer is located in a joint portion of the needle-shaped projection and the support base.

6. A needle-shaped body, comprising:
a needle-shaped projection; and
a support base which supports the needle-shaped projection,
wherein at least a portion of the needle-shaped projection comprises a projection side layer, at least a portion of the support base comprises a support base side layer, the projection side layer is formed directly on the support base side layer, the projection side layer comprises at least one material selected from the group consisting of pullulan and dextran, and the support base side layer comprises at least one material selected from the group consisting of hydroxypropyl cellulose, hydroxyethyl cellulose, methyl cellulose, and hydroxypropyl methyl cellulose.

7. The needle-shaped body according to claim 6, wherein the support base side layer and a portion of the projection side layer form the support base.

8. The needle-shaped body according to claim 7, wherein the portion of the projection side layer in the support base has a smaller area than an outer shape of the support base.

9. The needle-shaped body according to claim 6, wherein the projection side layer and a portion of the support base side layer form the needle-shaped projection.

10. The needle-shaped body according to claim 6, wherein the projection side layer and the support base side layer are formed such that a boundary of the projection side layer and the support base side layer is located in a joint portion of the needle-shaped projection and the support base.

11. The needle-shaped body according to claim 6, wherein the projection side layer comprises the at least one material selected from the group consisting of pullulan and dextran and the support base side layer comprises the at least one material selected from the group consisting of hydroxypropyl cellulose, hydroxyethyl cellulose, methyl cellulose and hydroxypropyl methyl cellulose such that peeling strength between the projection side layer and the support base side layer is 8 N/15 mm in width or lower.

* * * * *